United States Patent
Durocher et al.

(10) Patent No.: US 12,109,591 B2
(45) Date of Patent: Oct. 8, 2024

(54) ULTRASOUND TRANSDUCER ARRAY ARCHITECTURE AND METHOD OF MANUFACTURE

(71) Applicant: GE Precision Healthcare LLC, Wauwatosa, WI (US)

(72) Inventors: Kevin Mathew Durocher, Troy, NY (US); Warren Lee, Niskayuna, NY (US); James Wilson Rose, Niskayuna, NY (US)

(73) Assignee: GE Precision Healthcare LLC, Waukesha, WI (US)

( * ) Notice: Subject to any disclaimer, the term of this patent is extended or adjusted under 35 U.S.C. 154(b) by 278 days.

(21) Appl. No.: 16/565,219

(22) Filed: Sep. 9, 2019

(65) Prior Publication Data

US 2021/0069749 A1    Mar. 11, 2021

(51) Int. Cl.
    *B06B 1/06*     (2006.01)
    *A61B 8/00*     (2006.01)

(52) U.S. Cl.
    CPC .......... *B06B 1/0685* (2013.01); *A61B 8/4494* (2013.01); *B06B 1/0607* (2013.01);
    (Continued)

(58) Field of Classification Search
    CPC ..... A61B 8/4494; A61B 8/445; A61B 8/4411; A61B 2560/0443; A61B 8/54;
    (Continued)

(56) References Cited

U.S. PATENT DOCUMENTS

| | | |
|---|---|---|
| 4,576,045 A | 3/1986 | Miller-Jones |
| 4,612,809 A | 9/1986 | Cribbs et al. |

(Continued)

FOREIGN PATENT DOCUMENTS

| | | |
|---|---|---|
| EP | 0388438 A1 | 9/1990 |
| EP | 0779108 B1 | 2/2000 |
| EP | 2267481 A1 | 12/2010 |
| EP | 2267482 A1 | 12/2010 |
| JP | 0426418 A | 1/1992 |
| JP | 07322397 A | 12/1995 |
| JP | 0879895 A | 3/1996 |
| JP | 0889505 A | 4/1996 |
| JP | 11128225 A | 5/1999 |

(Continued)

OTHER PUBLICATIONS

PCT Search Report and Written Opinion from corresponding PCT Application No. PCT/US2014/051465 dated Jun. 10, 2015.

(Continued)

*Primary Examiner* — Sean D Mattson
*Assistant Examiner* — Michael Yiming Fang
(74) *Attorney, Agent, or Firm* — McAndrews, Held & Malloy, Ltd.; Daniel Bissing; David Bates

(57) ABSTRACT

An ultrasound transducer array architecture and manufacturing method is provided. The method includes providing an ultrasonic transducer including a plurality of modules, each module including an ultrasonic transducer array and an application specific integrated circuit (ASIC), the ultrasonic transducer array and the ASIC electrically coupled to a flexible interconnect, the flexible interconnect coupled to a connector. The ASIC and flexible interconnect may be arranged such that each ultrasonic transducer array is directly adjacent to another ultrasonic transducer array. The ASIC may be electrically coupled to the flexible interconnect and the ASIC to the transducer array via a redistribution layer. Each of the plurality of modules may be a stack with the ultrasonic transducer array on the RDL and RDL on the ASIC, wherein the flexible interconnect extends laterally from a top surface of the ASIC and curves down to a bottom surface of the ASIC.

23 Claims, 7 Drawing Sheets

(52) U.S. Cl.
CPC ............ *A61B 8/4411* (2013.01); *A61B 8/445* (2013.01); *B06B 2201/76* (2013.01)

(58) Field of Classification Search
CPC ... A61B 8/5207; A61B 8/4488; B06B 1/0685; B06B 1/0607; B06B 2201/76; B06B 1/0292; B06B 1/0622; H05K 1/00; H05K 2201/10151; H01L 27/00; H01L 31/00
See application file for complete search history.

(56) References Cited

U.S. PATENT DOCUMENTS

| | | | |
|---|---|---|---|
| 4,759,372 | A | 7/1988 | Umemura et al. |
| 4,915,115 | A | 4/1990 | Sasaki et al. |
| 4,953,147 | A | 8/1990 | Cobb |
| 5,044,053 | A | 9/1991 | Kopel et al. |
| 5,060,652 | A | 10/1991 | Umemura et al. |
| 5,353,797 | A | 10/1994 | Matsushima et al. |
| 5,617,866 | A | 4/1997 | Marian, Jr. |
| 5,722,412 | A | 3/1998 | Pflugrath |
| 5,820,549 | A | 10/1998 | Marian, Jr. |
| 5,876,344 | A | 3/1999 | Baker et al. |
| 6,080,109 | A | 6/2000 | Baker et al. |
| 6,524,254 | B2 | 2/2003 | Erikson et al. |
| 6,540,682 | B1 | 4/2003 | Leavitt et al. |
| 6,546,803 | B1 | 4/2003 | Ptchelintsev et al. |
| 6,602,197 | B2 | 8/2003 | Tahara |
| 6,618,916 | B1 | 9/2003 | Eberle et al. |
| 6,641,534 | B2 | 11/2003 | Smith et al. |
| 6,712,767 | B2 | 3/2004 | Hossack et al. |
| 6,757,948 | B2 | 7/2004 | Ptchelintsev et al. |
| 6,783,493 | B2 | 8/2004 | Chiang et al. |
| 6,859,984 | B2 | 3/2005 | Dinet et al. |
| 6,866,635 | B2 | 3/2005 | Dinet et al. |
| 7,081,093 | B2 | 7/2006 | Flesch |
| 7,285,897 | B2 | 10/2007 | Fisher et al. |
| 7,441,321 | B2 | 10/2008 | Baumgartner et al. |
| 7,445,766 | B2 | 11/2008 | Santini, Jr. et al. |
| 7,451,651 | B2 | 11/2008 | Woychik et al. |
| 7,491,172 | B2 | 2/2009 | Buestle |
| 7,494,469 | B2 | 2/2009 | Bruestle |
| 7,497,828 | B1 | 3/2009 | Wilk et al. |
| 7,557,489 | B2 | 7/2009 | Petersen et al. |
| 7,597,665 | B2 | 10/2009 | Wilk et al. |
| 7,617,732 | B2 | 11/2009 | Bui et al. |
| 7,739,913 | B2 | 6/2010 | Oosawa |
| 7,741,756 | B2 | 6/2010 | Sudol |
| 7,821,180 | B2 | 10/2010 | Kunkel, III et al. |
| 7,836,768 | B2 | 11/2010 | Young et al. |
| 7,867,824 | B2 | 1/2011 | Fisher et al. |
| 7,892,176 | B2 | 2/2011 | Wodnicki et al. |
| 7,927,280 | B2 | 6/2011 | Proulx et al. |
| 2002/0135282 | A1 | 9/2002 | Hudak |
| 2003/0018265 | A1 | 1/2003 | Tahara |
| 2003/0187349 | A1 | 10/2003 | Kaneko et al. |
| 2004/0054287 | A1 | 3/2004 | Stephens et al. |
| 2005/0075572 | A1 | 4/2005 | Mills et al. |
| 2005/0146247 | A1 | 7/2005 | Fischer et al. |
| 2005/0154314 | A1 | 7/2005 | Quistgaard |
| 2005/0169107 | A1 | 8/2005 | Thomenius et al. |
| 2005/0203412 | A1 | 9/2005 | Amemiya |
| 2006/0173333 | A1 | 8/2006 | Sudol |
| 2006/0241479 | A1 | 10/2006 | Wada |
| 2006/0281045 | A1 | 12/2006 | Ariff et al. |
| 2007/0016064 | A1 | 1/2007 | Yamashita et al. |
| 2008/0089538 | A1 | 4/2008 | Ono |
| 2008/0106976 | A1 | 5/2008 | Davidsen et al. |
| 2008/0200813 | A1 | 8/2008 | Quistgaard |
| 2008/0273424 | A1 | 11/2008 | Wodnicki et al. |
| 2008/0315331 | A1* | 12/2008 | Wodnicki ............ G01S 7/52079 257/414 |
| 2008/0315724 | A1 | 12/2008 | Kunkel, III |
| 2009/0028211 | A1 | 1/2009 | Amemiya |
| 2009/0043206 | A1 | 2/2009 | Towfiq et al. |
| 2009/0093719 | A1 | 4/2009 | Pelissier et al. |
| 2009/0105596 | A1 | 4/2009 | Savord et al. |
| 2009/0306518 | A1 | 12/2009 | Kurse et al. |
| 2010/0036257 | A1* | 2/2010 | Sano .................... A61B 8/4281 600/459 |
| 2010/0156243 | A1 | 6/2010 | Weekamp et al. |
| 2010/0171395 | A1 | 7/2010 | Cannanta et al. |
| 2010/0256488 | A1 | 10/2010 | Kim et al. |
| 2010/0327173 | A1* | 12/2010 | Woychik ................. H01L 25/16 438/66 |
| 2011/0034809 | A1 | 2/2011 | Eberle et al. |
| 2011/0071397 | A1 | 3/2011 | Wodnicki et al. |
| 2011/0144544 | A1 | 6/2011 | Fan et al. |
| 2011/0208355 | A1 | 8/2011 | Su |
| 2011/0218441 | A1 | 9/2011 | Osawa |
| 2011/0301464 | A1 | 12/2011 | Yoo et al. |
| 2012/0133001 | A1* | 5/2012 | Tkaczyk ............... A61B 8/4483 257/414 |
| 2012/0143063 | A1 | 6/2012 | Robinson |
| 2012/0267981 | A1 | 10/2012 | Morris et al. |
| 2013/0270682 | A1* | 10/2013 | Hu .......................... H01L 24/81 257/E21.705 |
| 2013/0345567 | A1 | 12/2013 | Sudol |
| 2015/0087988 | A1* | 3/2015 | Lee ...................... A61B 8/4494 600/459 |
| 2015/0305713 | A1* | 10/2015 | Kim ..................... B06B 1/0629 600/459 |
| 2017/0188995 | A1* | 7/2017 | Bruestle ................ B06B 1/0685 |
| 2017/0238902 | A1* | 8/2017 | Lee ...................... A61B 8/4455 |
| 2018/0368805 | A1* | 12/2018 | Hadjicostis .......... A61B 8/0891 |

FOREIGN PATENT DOCUMENTS

| | | |
|---|---|---|
| JP | 2000354596 A | 12/2000 |
| JP | 2000354597 A | 12/2000 |
| JP | 2002306489 A | 10/2002 |
| JP | 2006247025 A | 9/2006 |
| JP | 2007007262 A | 1/2007 |
| JP | 2007288704 A | 11/2007 |
| JP | 2007307288 A | 11/2007 |
| JP | 2008093222 A | 4/2008 |
| JP | 2008187625 A | 8/2008 |
| JP | 2009022679 A | 2/2009 |
| JP | 2010194013 A | 9/2010 |
| WO | 2005055832 A1 | 6/2005 |
| WO | 2006105476 A2 | 10/2006 |
| WO | 2009042867 A1 | 4/2009 |
| WO | 2009149315 A2 | 12/2009 |

OTHER PUBLICATIONS

PCT Invitation For Corresponding PCT Application No. PCT/US2014/051465 dated Apr. 2, 2015.

* cited by examiner

ULTRASOUND TRANSDUCER ARRAY ARCHITECTURE AND METHOD OF MANUFACTURE

FIELD

Certain embodiments relate to ultrasound imaging. More specifically, certain embodiments relate to an ultrasound transducer array architecture and manufacture.

BACKGROUND

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images. Ultrasound transducers convert ultrasonic signals to electrical signals and/or convert electrical signals to ultrasonic signals.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

An ultrasound transducer array architecture and manufacturing methods are provided, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
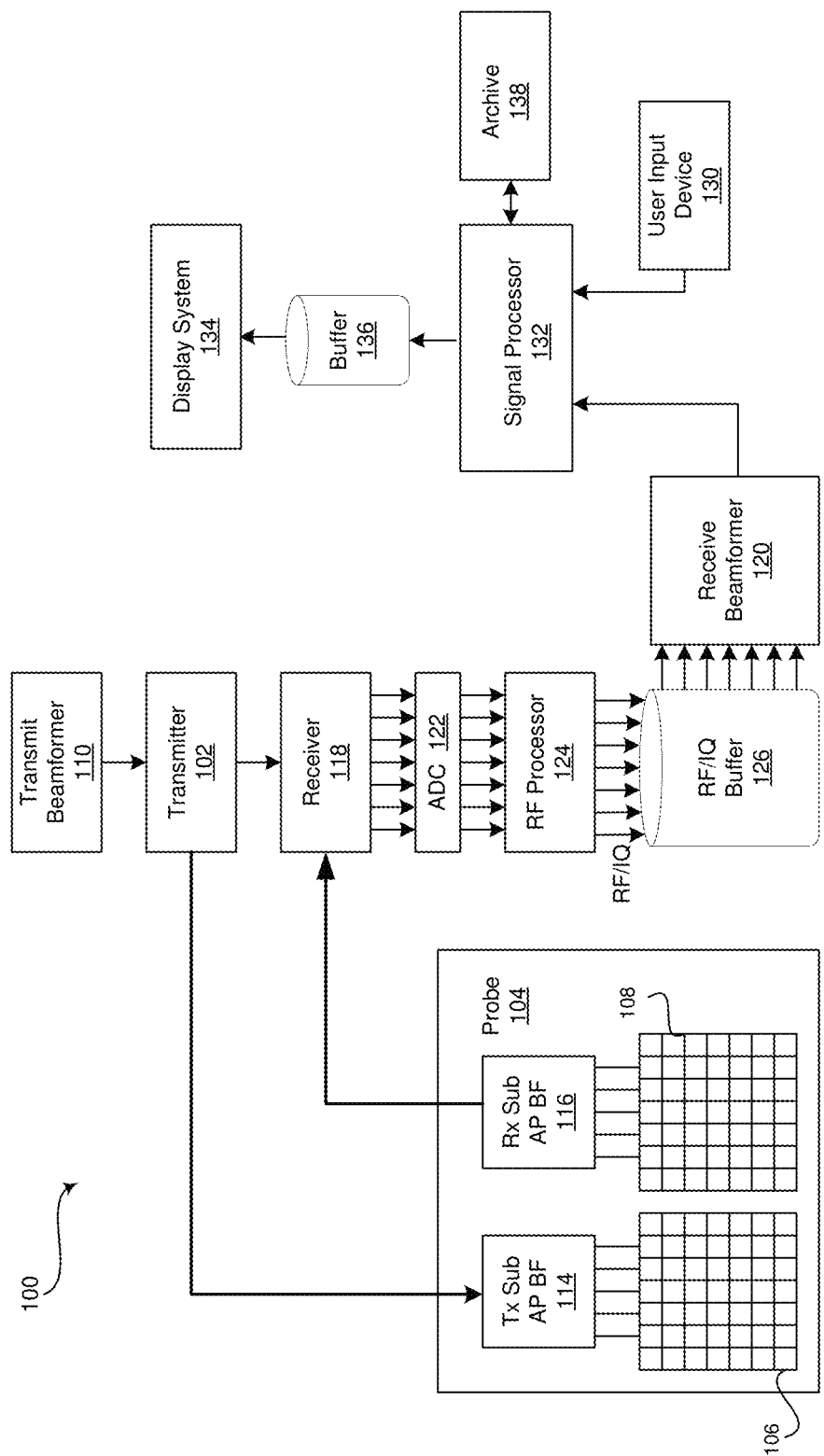
FIG. 1 is a block diagram of an example ultrasound system that is operable to perform an ultrasound examination, in accordance with various embodiments.

Certain embodiments may be found in an ultrasound transducer array architecture and manufacturing methods. The system may comprise an ultrasonic transducer comprising a plurality of modules, each module comprising an ultrasonic transducer array and an application specific integrated circuit (ASIC), the transducer array and the ASIC electrically coupled to a flexible interconnect, and the flexible interconnect coupled to a connector. The ASIC and flexible interconnect may be arranged such that each ultrasonic transducer array is directly adjacent to another ultrasonic transducer array.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, application specific integrated circuit (ASIC) or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having tileable transducer arrays in accordance with various embodiments is illustrated in FIG. 1.

FIG. 1 is a block diagram of an example ultrasound system 100 that is operable to perform an ultrasound examination, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a one-dimensional (1D) or two-dimensional (2D) array of capacitive micromachined ultrasonic transducers (cMUTs), piezo micromachined ultrasonic transducers (pMUTs), or traditional piezoelectric transducers. The ultrasound probe 104 may comprise a group of transmit transducer elements 106 and a group of receive transducer elements 108, that normally constitute the same elements.

In an example embodiment, the transmit transducer elements 106 and the receive transducer elements 108 may comprise tileable arrays, each with its own ASIC, optional redistribution layer (RDL), flexible interconnect, and connector for coupling to circuitry of a transmit sub-aperture beamformer 114 and a receive sub-aperture beamformer 116, for example. By arranging tileable array modules capable of being directly arranged adjacent to each other on all four sides without significant gaps between, large-sized transducer arrays may be achieved with individually testable modules prior to assembly, greatly improving yields and lowering costs. In an example embodiment, the transducer arrays may define the largest area of each module, so that each may be placed directly adjacent without gaps that can reduce transducer resolution. Furthermore, if an individual transducer module fails, it may be replaced without having to replace the entire transducer.

In certain embodiments, the ultrasound probe 104 may be operable to acquire ultrasound image data covering at least a substantial portion of an anatomy, such as the heart, a blood vessel, or any suitable anatomical structure.

The transmit beamformer 110 may comprise suitable logic, circuitry, interfaces and/or code that may be operable to control the transmitter 102 which, through the transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by the receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to the RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may be capable of receiving input information from a user input device 130 and/or archive 138, generating an output displayable by a display system 134, and manipulating the output in response to input information from a user input device 130, among other things.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The display system 134 may be any device capable of communicating visual information to a user. For example, a display system 134 may include a liquid crystal display, a light emitting diode display, and/or any suitable display or displays. The display system 134 can be operable to present ultrasound images and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Figure 2:
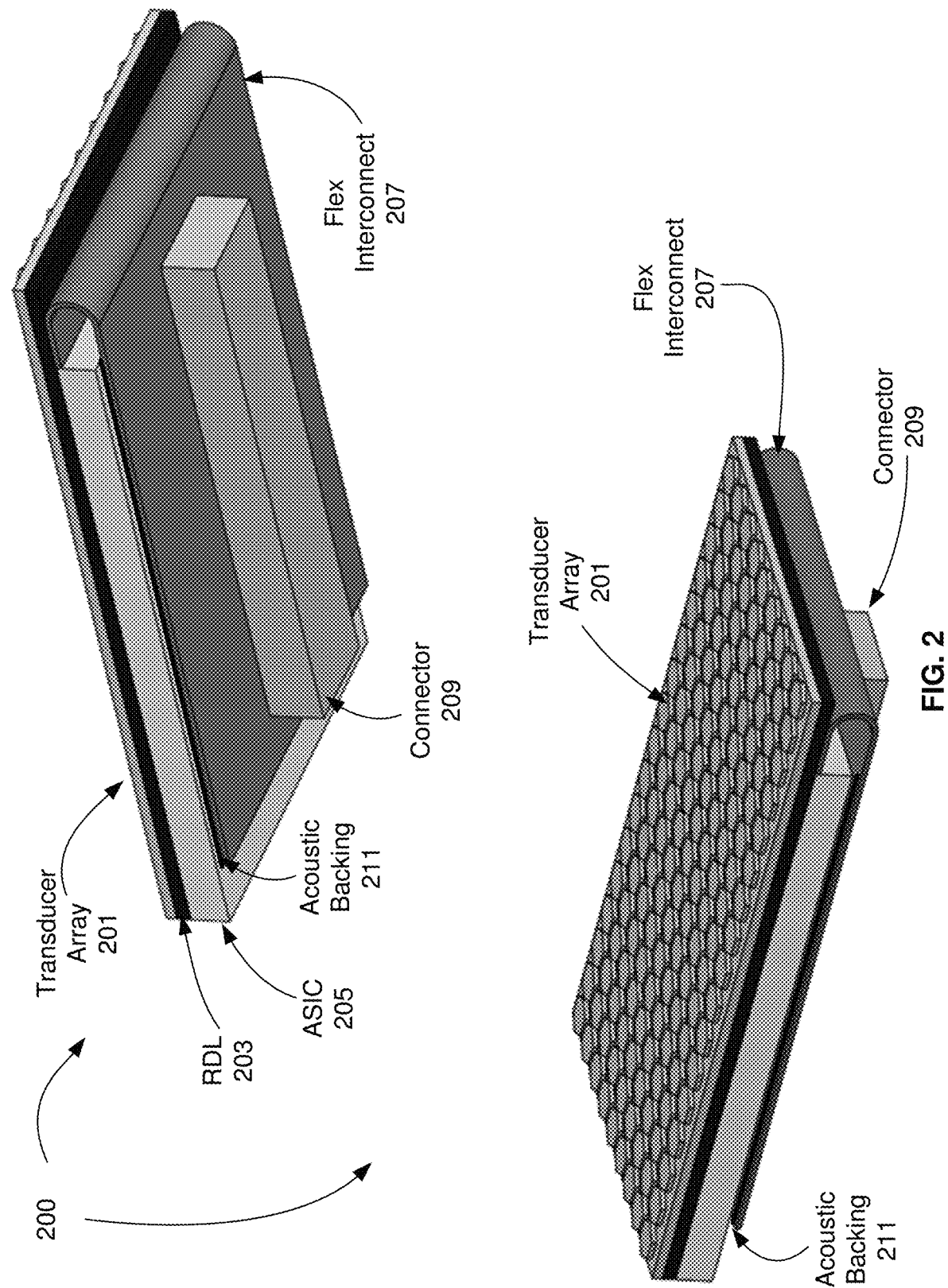
FIG. 2 illustrates oblique angle views of an individual tileable transducer module, in accordance with various embodiments.

FIG. 2 illustrates oblique angle views of an individual tileable transducer module, in accordance with various embodiments. Referring to FIG. 2, there is shown transducer module 200 comprising a transducer array 201, an RDL 203, an ASIC 205, a flex interconnect 207, a connector 209, and acoustic backing 211. In one embodiment, the transducer array 201 may comprise an array of cMUT, pMUT, or traditional piezoelectric elements where micromachined elements may be actuated by ultrasonic signals in a receive mode, or may generate an ultrasonic signal when driven by an appropriate electrical signal, in a transmit mode. An example material for cMUT elements is silicon. In another example embodiment, the transducer array 201 may comprise an array of piezoelectric elements, where piezoelectric materials mechanically vibrate, and thus generate ultrasonic signals, when a voltage is applied, or conversely generate an electrical signal when an ultrasonic signal impinges on the material.

The RDL 203 may comprise a plurality of conductive traces and insulating material for providing electrical contact between the transducer array 201 and the ASIC 205, sometimes referred to as an interposer. For example, contacts on the ASIC 205 may not have the same location as those on the transducer array 201, and the use of the RDL 203 enables the interconnection of these devices without having to design them with identical placement of contacts. However, if the contacts on the transducer array 201 and the ASIC 205 do have the same placement, the RDL 203 may be eliminated.

The ASIC 205 may comprise circuitry for driving and/or receiving signals from the transducer 201 and therefore may comprise processing, amplification, transmission, and receiver circuitry, for example. For example, the ASIC 205 may provide electrical signals to the elements cMUT or piezoelectric elements in the transducer array 201 to generate ultrasonic signals, or may receive electrical signals from the transducer array 201 when exposed to ultrasonic signals.

The flex interconnect 207 may comprise a flat flexible electrical interconnection device comprising conductive traces within flexible insulating material, such as polyimide, for example. In this manner, electrical signals may be communicated between the connector 209 and the ASIC 205 with a flexible and configurable physical connector. Although the flex interconnect 207 is shown as only extending out from one side of the module, the disclosure is not so limited, as the interconnect 207 may extend from one or more sides of the module and/or completely across the ASIC 205 and/or RDL 203, depending on the desired configuration. In this example scenario where the flex interconnect 207 extends all the way across the module, there may be straight pass-through connections through the interconnect 207 from the ASIC 205 to the RDL 203.

The connector 209 may comprise an electrical and mechanical connector for the transducer module 200, where electrical signals may be communicated between the module 200 and external circuitry. In addition, the connector 209 may mechanically affix the transducer module 200 to a supporting structure such as a printed circuit board or other suitable substrate.

The module 200 may be designed to occupy a footprint equal to, or smaller than the active area of the 2D transducer array 201, thus allowing the tiling of additional modules on all four sides of a given module without significant gaps in the larger, overall tiled 2D transducer array. The transducer module 200 may contain acoustic backing 211 underneath the ASIC to provide isolation from the ultrasonic signals.

Figure 3:
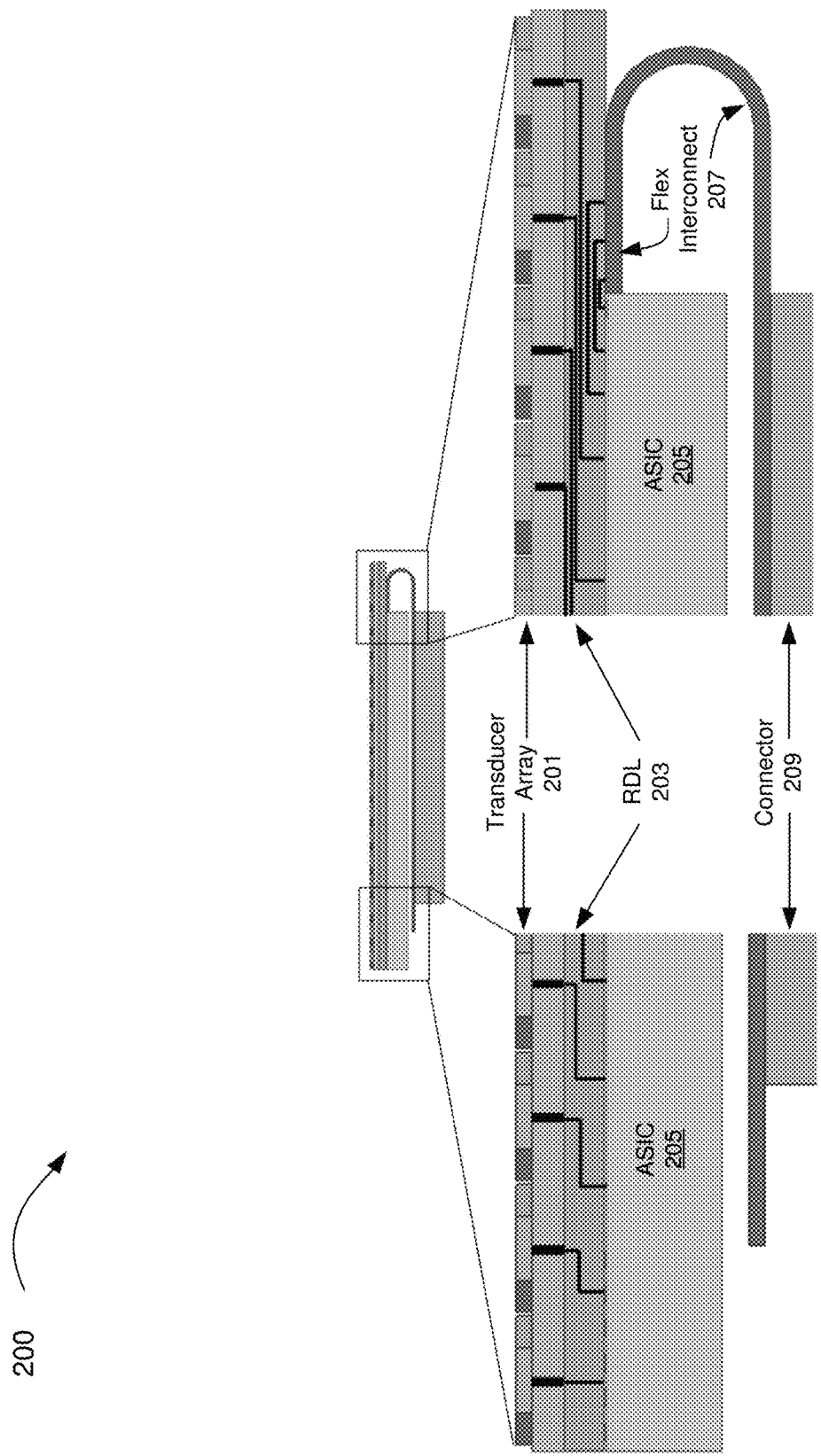
FIG. 3 illustrates a cross-sectional view of a tileable transducer module, in accordance with various embodiments.

FIG. 3 illustrates a cross-sectional view of a tileable transducer module, in accordance with various embodiments. Referring to FIG. 3, there is shown cutaway views of transducer module 200 showing the left and right edges of the structure as indicated by the inset boxes. As described with respect to FIG. 2, the transducer module 200 may comprise the transducer array 201, the RDL 203, the ASIC 205, the flex interconnect 207, and the connector 209. As indicated by the horizontal and vertical lines in the RDL 203, the RDL 203 provides electrical routing between contacts on the ASIC 205, the transducer array 201, and the flex interconnect 207. In the left inset, the RDL 203 couples the transducer array to the ASIC 205, and in the right inset, the RDL 203 provides electrical connection between the transducer array 201 and the ASIC 205 as well as between the ASIC 205 and the flex interconnect 207.

The interconnect pitch of the ASIC 205 and transducer array 201 may be different, and adapted to each other through the RDL 203. The RDL 203 may also route I/O (such as power, control lines, digital and analog signals) from the ASIC 205 to the flex interconnect 107. The connector 209 on the flex interconnect 207 allows for interconnection of the module to the ultrasound system. Another embodiment may comprise coupling the transducer array 201 directly on the ASIC 205 when the contacts on the ASIC 205 and the transducer array 201 directly align, removing the need for the RDL 203. In another embodiment, the transducer array 201 may be fabricated directly on the ASIC 205, such as through a surface micromachining build up process, for example.

Figure 4:
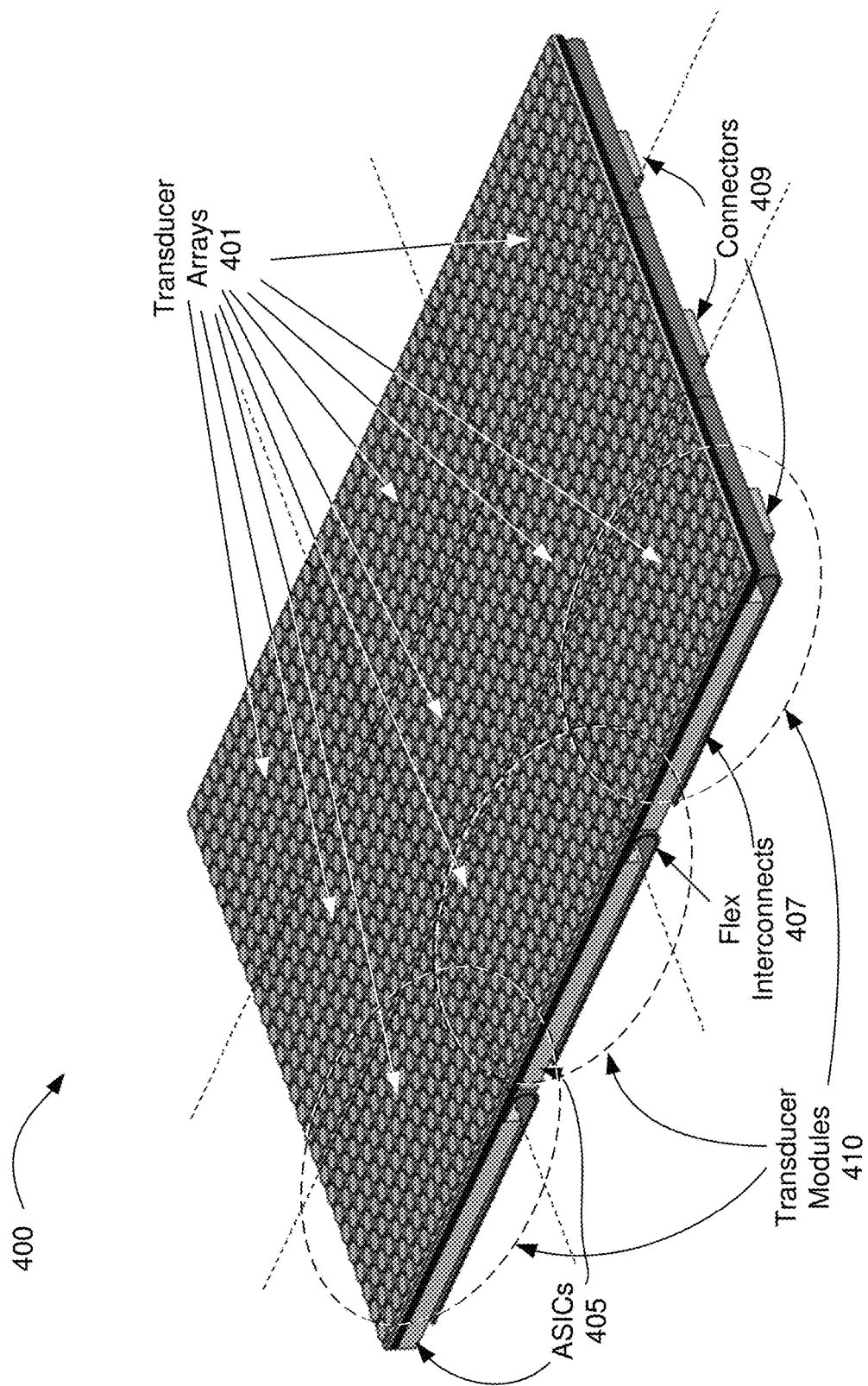
FIG. 4 illustrates individual transducer modules tiled in a 2-dimensional matrix, in accordance with various embodiments.

FIG. 4 illustrates individual transducer modules tiled in a 2-dimensional matrix, in accordance with various embodiments. Referring to FIG. 4, there is shown a transducer 400 comprising a plurality of transducer array modules 410 where each of the modules 410 comprises a transducer array 401, an ASIC 405, a flex interconnect 407, and a connector 409.

The dashed lines in FIG. 4 indicate the boundaries between individual transducer array modules 401. Since each module is designed to occupy a footprint equal to, or smaller than the active area of the transducer array, multiple modules may be tiled in a matrix array pattern forming a larger continuous matrix array without significant gaps in between the tiled modules, where gaps could reduce the resolution of the transducer.

Figure 5:
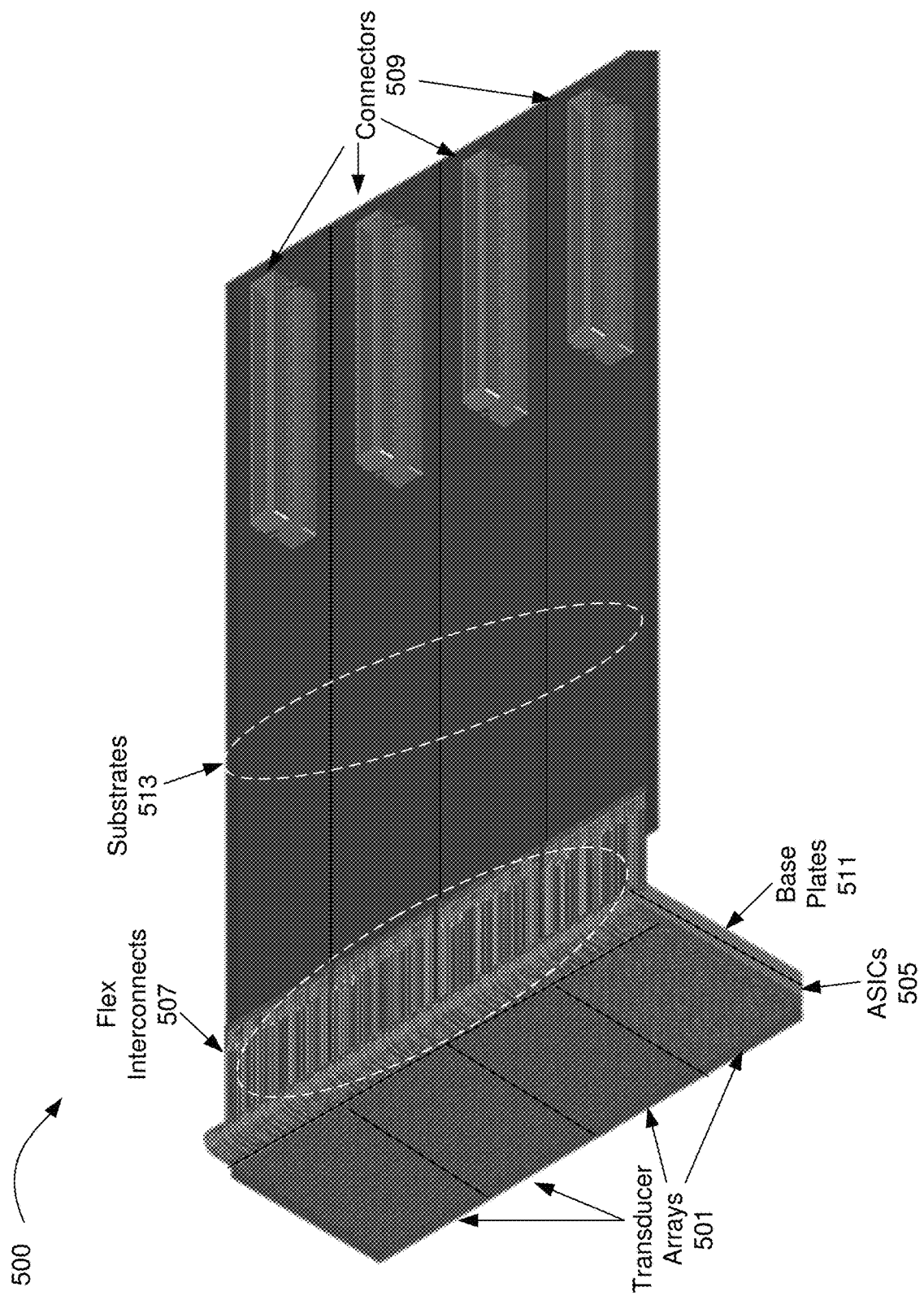
FIG. 5 illustrates a 1×4 transducer array, in accordance with various embodiments.

FIG. 5 illustrates a 1×4 transducer array, in accordance with various embodiments. Referring to FIG. 5, there is shown 1×4 array 500 comprising four transducer arrays 501, four ASICs 505, four flex interconnects 507, four connectors 509, base plates 511, and substrates 513. This embodiment allows for a different orientation of the transducer arrays with respect to the connectors 509. The transducer arrays 501, ASICs 505, flex interconnects 507, and connectors 509 may be as described previously, while the base plates 511 may comprise rigid support structures, such as metal plates, that provide support to the transducer arrays 501 and ASICs 505. The base plates 511 may also provide accurate alignment of each module of the 1×4 array 500 with alignment pins, for example, as shown in FIG. 6.

The substrates 513 may comprise a rigid structure for mechanical support as well as continuation of electrical connectivity between the flex interconnects 507 and the connectors 509, and in one example comprises printed circuit boards (PCBs) formed from conductive traces in a glass-reinforced epoxy laminate material, such as FR4. Other suitable substrates may comprise ceramic and/or high temperature dielectric materials, for example. In addition, a separate acoustic backing layer may be incorporated underneath the transducer arrays 501, such as between the ASICs 505 and base plates 511, for example, as illustrated in FIG. 2

Some novel aspects of this configuration include the accommodation of transducer arrays 501 arranged in a 1D array and an arbitrary radius built into the base plate 511 for a relaxed flex bend in the flex interconnects 507. Alternatively, with a 2D array, the radius of the base plate 511 may be configured to support a tight flex wrap in the flex interconnects 507. Similar to that shown in FIGS. 2-4. In addition, the use of PCBs for the substrates 513 enables the simpler incorporation of passives and connectors, as opposed to directly placing these devices on flex material, which can increase cost and complexity. The substrates 513 also allow a reduction in layer count of the flex interconnects 507.

Figure 6:
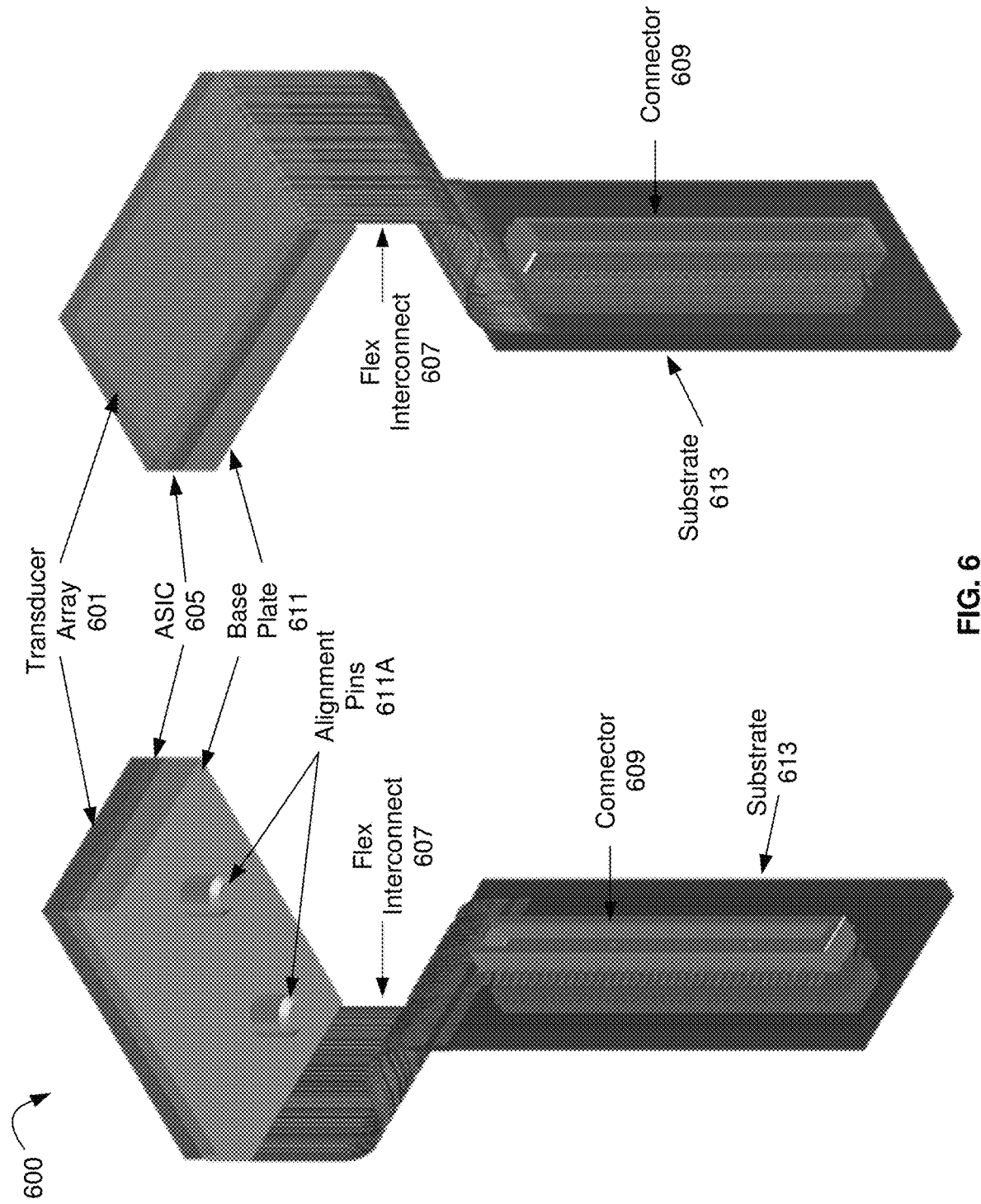
FIG. 6 illustrates a 2D transducer array, in accordance with various embodiments.

FIG. 6 illustrates a 2D transducer array, in accordance with various embodiments. Referring to FIG. 6, there is shown 2D array 600 module comprising transducer array 601, ASIC 605, flex interconnect 607, connector 609, base plate 611, and substrates 613, which may be similar to as described previously. In addition, the base plate 611 comprises alignment pins 611A for accurate alignment of the 2D array module 600 with a base plate (not shown) in the ultrasound system. The base plate 611 may be machined from aluminum to optimize heat transport and/or may be molded from a composite material to optimize acoustic properties.

This configuration enables an orthogonal arrangement between the transducer arrays and the connectors. The alignment pins 611A and the flat, coplanar surface of the base plate 611 facilitate 1D and 2D assembly. Furthermore, this allows for pretesting of the ASICs and the transducer arrays prior to bonding and assembly, which reduces costs and improves system yields. Similarly, individual arrays may be swapped out upon failure, improving serviceability of the transducer array. A base plate (not shown), to which the alignment pins 611A are inserted, may determine the position of each backer, which may enable the configuration of any precisely positioned array desired, and the tiling could include offsets between adjacent rows if desired. The alignment pins 611A and/or notches or pins in the transducer array 601, ASIC 605, and or base plate 611 may enable "keying" in the accurate and precise arrangement of the modules in a plurality of modules.

Figure 7:
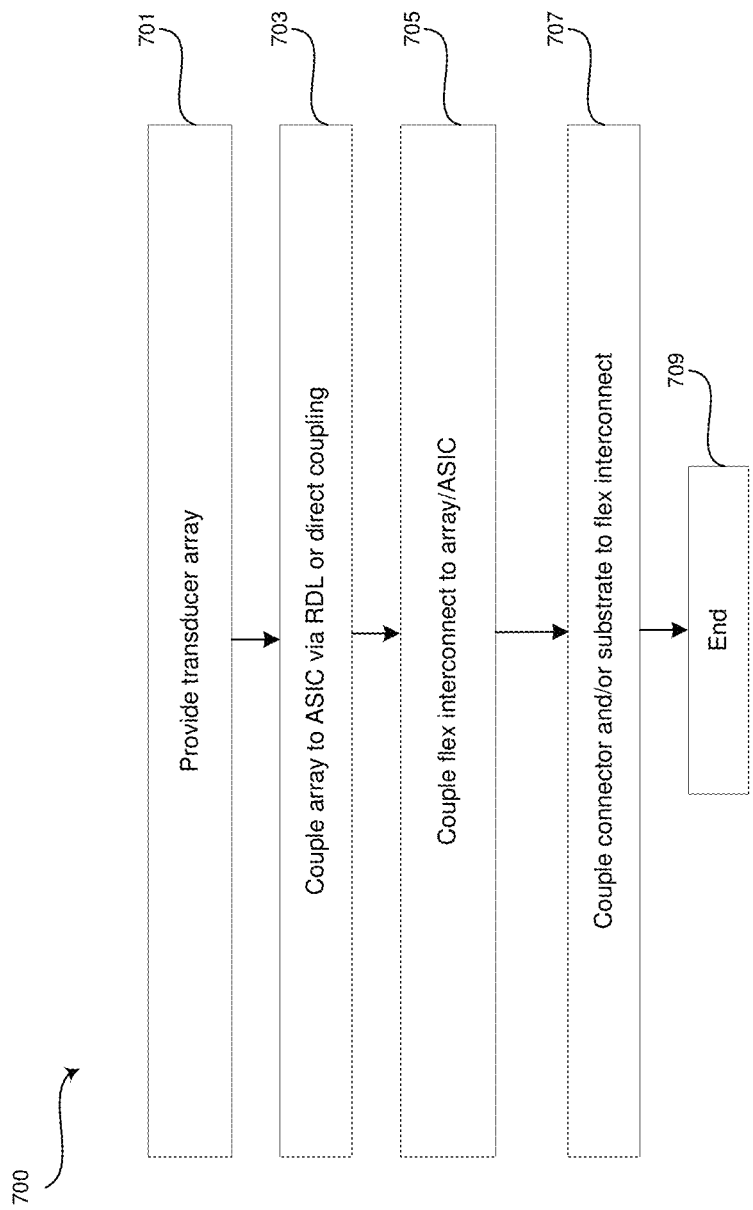
FIG. 7 is a flow chart illustrating example steps for fabricating a tiled ultrasonic transducer array, in accordance with various embodiments.

FIG. 7 is a flow chart illustrating example steps for fabricating a tiled ultrasonic transducer array, in accordance with various embodiments. Referring to FIG. 7, there is shown a flow chart 700 comprising exemplary steps 701 through 709. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 701, a transducer array may be provided and coupled to an ASIC via an optional RDL in step 703. In another example embodiment, the transducer array may be coupled directly to, in instances where the contacts on the ASIC and transducer array directly align, or fabricated directly on the ASIC. In step 705, the transducer array/RDL/ASIC may be coupled to a flex interconnect, followed by step 707 where a connector may be coupled to the flex interconnect. In another example embodiment, a substrate may be coupled to the flex interconnect, where the substrate comprises the connector.

The above process enables system advantages including unique tiling for obtaining registration and spacing of modules to form a large sensor footprint. The incorporation of flexible substrates and RDLs/interposers are also disclosed as well as the ability to "key" tiles for optimum registration and alignment of adjacent tiles or modules. This tiling concept allows for high packing density and minimal loss of active area sensing.

In addition, the tiled arrays allow for optimized packing density of interconnects and tiles to minimize loss of active area imaging and electrical and mechanical issues related to conventional interconnects. Alignment features may be utilized for tiling into the heat sink and/or the backing material, which may eliminate the need to generate a costly carrier that has to be micro-machined out of silicon or metal.

Furthermore, the tiled arrays allow for low cost lightweight assemblies. Modular tiling allows for pre-testing of portions of the completed device to streamline production, reduce scrap, and allow for module replacements if defective. The configurations described above allow for a sensor footprint of optimized tiling without significant gaps. The assembly processes also include regions for redistribution layers and electronics integration. These design concepts enable pretesting of electronic interconnection of both the flex circuit and ASIC, along with the possible combination of the sensor array. The concepts described above also enable key alignment and registration as well as integration of backing and heat sink materials.

Aspects of the present disclosure provide a method and system for an ultrasound transducer array architecture and manufacture. The method includes providing an ultrasonic transducer comprising a plurality of modules, each module comprising an ultrasonic transducer array and an application specific integrated circuit (ASIC), the ultrasonic transducer array and the ASIC electrically coupled to a flexible interconnect, the flexible interconnect coupled to a connector. The ASIC and flexible interconnect may be arranged such that each ultrasonic transducer array is directly adjacent to another ultrasonic transducer array. The ASIC may be electrically coupled to the flexible interconnect and the ASIC to the transducer array via a redistribution layer.

Each of the plurality of modules may comprise a stack with the ultrasonic transducer array on the RDL and RDL on the ASIC, wherein the flexible interconnect extends laterally from a top surface of the ASIC or bottom surface of the RDL and curves down to a bottom surface of the ASIC. The connector may be coupled to a bottom surface of the flexible interconnect. Each of the plurality of modules may comprise a stack comprising the ultrasonic transducer array, the ASIC, and a base plate, wherein the flexible interconnect extends from the stack to a substrate comprising the connector. The substrate may comprise a printed circuit board. The substrate may be orthogonal to the stack. The base plate may comprise a metal or composite plate with alignment pins. The ultrasonic transducer array may comprise capacitive micromachined ultrasonic transducers (cMUT), piezo micromachined ultrasonic transducers (pMUTs), or traditional piezoelectric transducers. Because this module structure may be used in different ultrasound imaging applications due to the RDL adapting the pitch of ASIC connections to different transducer array pitches and overall array sizes, significant cost savings are enabled.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
providing an ultrasonic transducer comprising a plurality of modules, each module comprising an ultrasonic transducer array, a flexible interconnect, a connector, and an application specific integrated circuit (ASIC), a top surface of the ASIC electrically coupled to the flexible interconnect at a first interconnect end, the flexible interconnect extending laterally from the top surface of the ASIC and curving around a first lateral side of the ASIC to a second interconnect end directly vertically below a bottom surface of the ASIC and between the first lateral side and a second lateral side of the ASIC, the flexible interconnect coupled to the connector below the bottom surface of the ASIC, wherein:
a footprint of the ASIC is smaller than a footprint of the ultrasonic transducer array, and
the ASIC and the flexible interconnect are arranged such that the ultrasonic transducer array of each module of the plurality of modules is directly adjacent to another ultrasonic transducer array of another one of the plurality of modules.

2. The method of claim 1, wherein:
each of the plurality of modules comprises a redsitribution layer (RDL) between the ultrasonic transducer array and the ASIC, and
the RDL electrically couples both:
the ASIC directly to the flexible interconnect, and
the ASIC directly to the ultrasonic transducer array.

3. The method of claim 2, wherein each of the plurality of modules comprises a stack with the ultrasonic transducer array on the RDL and the RDL on the ASIC.

4. The method of claim 3, wherein the connector is coupled to a bottom surface of the flexible interconnect between the first interconnect end and the second interconnect end.

5. The method of claim 1, wherein each of the plurality of modules comprises a stack comprising the ultrasonic transducer array on the ASIC, and the ASIC on a base plate, wherein the flexible interconnect extends from the stack to a substrate comprising the connector.

6. The method of claim 5, wherein the substrate comprises a printed circuit board.

7. The method of claim 5, wherein the substrate is orthogonal to the stack.

8. The method of claim 5, wherein the base plate comprises a metal plate with alignment pins or a composite plate with the alignment pins.

9. The method of claim 1, wherein the ultrasonic transducer array comprises capacitive micromachined ultrasonic transducers (cMUT).

10. The method of claim 1, wherein the ultrasonic transducer array comprises piezoelectric transducers.

11. The method of claim 1, wherein an acoustic backing layer is beneath the bottom surface of the ASIC.

12. The method of claim 1, wherein the first interconnect end electrically coupled to the top surface of the ASIC is entirely below the ultrasonic transducer array.

13. A system comprising:
an ultrasonic transducer comprising a plurality of modules, each module comprising an ultrasonic transducer array, a flexible interconnect, a connector, and an application specific integrated circuit (ASIC), a top surface of the ASIC electrically coupled to the flexible interconnect at a first interconnect end, the flexible interconnect extending laterally from the top surface of the ASIC and curving around a first lateral side of the ASIC to a second interconnect end directly vertically below a bottom surface of the ASIC and between the first lateral side and a second lateral side of the ASIC, the flexible interconnect coupled to the connector below the bottom surface of the ASIC, wherein:
a footprint of the ASIC is smaller than a footprint of the ultrasonic transducer array, and
the ASIC and the flexible interconnect are arranged such that the ultrasonic transducer array of each module of the plurality of modules is directly adjacent to another ultrasonic transducer array of another one of the plurality of modules.

14. The system of claim 13, wherein:
each of the plurality of modules comprises a redistribution layer (RDL) between the ultrasonic transducer array and the ASIC, and
the RDL electrically couples both:
the ASIC directly to the flexible interconnect, and
the ASIC directly to the ultrasonic transducer array.

15. The system of claim 14, wherein each of the plurality of modules comprises a stack with the ultrasonic transducer array on the RDL and the RDL on the ASIC.

16. The system of claim 15, wherein the connector is coupled to a bottom surface of the flexible interconnect between the first interconnect end and the second interconnect end.

17. The system of claim 13, wherein each of the plurality of modules comprises a stack comprising the ultrasonic transducer array on the ASIC, and the ASIC on a base plate, wherein the flexible interconnect extends from the stack to a substrate comprising the connector.

18. The system of claim 17, wherein the substrate comprises a printed circuit board.

19. The system of claim 17, wherein the base plate comprises a metal plate with alignment pins or a composite plate with the alignment pins.

20. The system of claim 13, wherein the ultrasonic transducer array comprises capacitive micromachined ultrasonic transducers (cMUT).

21. The system of claim 13, wherein the ultrasonic transducer array comprises piezoelectric transducers.

22. The system of claim 13, wherein an acoustic backing layer is beneath the bottom surface of the ASIC.

23. The system of claim 13, wherein the first interconnect end electrically coupled to the top surface of the ASIC is entirely below the ultrasonic transducer array.

* * * * *